United States Patent
Hofmann et al.

(10) Patent No.: US 11,615,528 B2
(45) Date of Patent: Mar. 28, 2023

(54) METHOD AND DEVICE FOR COMPUTED TOMOGRAPHY IMAGING

(71) Applicant: Siemens Healthcare GmbH, Erlangen (DE)

(72) Inventors: Bernd Hofmann, Erlangen (DE); Florian Kuemmel, Hausen (DE); Kerstin Mueller, San Francisco, CA (US)

(73) Assignee: SIEMENS HEALTHCARE GMBH, Erlangen (DE)

( * ) Notice: Subject to any disclaimer, the term of this patent is extended or adjusted under 35 U.S.C. 154(b) by 294 days.

(21) Appl. No.: 16/924,550

(22) Filed: Jul. 9, 2020

(65) Prior Publication Data

US 2021/0019882 A1 Jan. 21, 2021

(30) Foreign Application Priority Data

Jul. 16, 2019 (DE) .......................... 102019210473.8

(51) Int. Cl.
  *G06T 7/00* (2017.01)
  *A61B 6/00* (2006.01)
  (Continued)

(52) U.S. Cl.
  CPC ............ *G06T 7/0012* (2013.01); *A61B 6/032* (2013.01); *A61B 6/4208* (2013.01); *A61B 6/501* (2013.01);
  (Continued)

(58) Field of Classification Search
  CPC ..... A61B 6/5258; A61B 6/583; A61B 6/4208; A61B 6/032; A61B 6/482; A61B 6/5217;
  (Continued)

(56) References Cited

U.S. PATENT DOCUMENTS 9,014,447 B2 * 4/2015 Slabaugh .............. G06T 7/0012
 382/128
10,492,749 B2 * 12/2019 Boone .................... A61B 6/488
(Continued)

OTHER PUBLICATIONS

Mohammed, M. F. et al: "Unenhanced Dual-Energy Computed Tomography. Visualization of brain edema"; in: Investigative Radiology; vol. 53; 2018; No. 2; pp. 63-69; ISSN: 0020-9996/17/0000-0000; DO1: 10. 1097/RLI.0000000000000413.
(Continued)

*Primary Examiner* — Irakli Kiknadze
(74) *Attorney, Agent, or Firm* — Harness, Dickey & Pierce, P.L.C.

(57) ABSTRACT

A method is for computed tomography imaging. In an embodiment, the method includes provisioning a CT data set of an object, the CT data set being previously recorded via a multispectral recording method; suppressing a contrast, caused by a tissue type, and generating a contrast-suppressed data set from the CT data set provisioned; and analyzing at least the contrast-suppressed data set generated or a data set generated via a machine learning algorithm based on the contrast-suppressed data set, the analyzing being configured to identify at least one change in the tissue type. A corresponding device, a control device for a computed tomography system or a diagnosis system, and a diagnosis system and a computed tomography system are also disclosed.

24 Claims, 2 Drawing Sheets

(51) Int. Cl.

| | |
|---|---|
| *G06T 11/00* | (2006.01) |
| *G16H 50/20* | (2018.01) |
| *G06N 3/08* | (2006.01) |
| *G06N 3/04* | (2006.01) |
| *A61B 6/03* | (2006.01) |

(52) U.S. Cl.
CPC .............. *A61B 6/5258* (2013.01); *A61B 6/54* (2013.01); *A61B 6/583* (2013.01); *G06N 3/04* (2013.01); *G06N 3/08* (2013.01); *G06T 11/008* (2013.01); *G16H 50/20* (2018.01); *A61B 6/507* (2013.01); *G06T 2207/10081* (2013.01); *G06T 2207/20081* (2013.01); *G06T 2207/20084* (2013.01); *G06T 2207/30016* (2013.01); *G06T 2211/408* (2013.01)

(58) Field of Classification Search
CPC ........... A61B 6/54; A61B 6/501; A61B 6/507; A61B 6/545; A61B 6/481; A61B 6/5223; A61B 6/505; A61B 6/40; A61B 6/5235; A61B 6/4035; A61B 8/5269; A61B 6/037; A61B 5/7203; A61B 5/055; A61B 6/03; A61B 5/7267; A61B 6/504; A61B 6/5205; A61B 8/5261; A61B 8/08; A61B 6/469; A61B 6/5247; A61B 6/463; A61B 6/4417; A61B 6/5294; A61B 6/466; A61B 2576/00; A61B 6/4241; A61B 2505/05; A61B 8/5223; A61B 5/4504; A61B 8/0875; A61B 6/542; A61B 6/503; A61B 6/486; A61B 6/4441; G16H 30/40; G16H 50/20; G16H 30/20; G16H 50/30; G16H 40/67; G16H 10/40; G06T 7/0012; G06T 11/008; G06T 2207/20081; G06T 2207/20084; G06T 2207/30016; G06T 2207/10081; G06T 2211/408; G06T 7/155; G06T 7/529; G06T 7/11; G06T 11/001; G06T 7/10; G06T 15/06; G06T 7/0014; G06T 2200/04; G06T 2207/30004; G06T 2207/10072; G06T 2207/30096; G06T 2207/30068; G06T 5/002; G06T 5/50; G06T 2207/10016; G06T 2207/30061; G06T 2207/10116; G06T 5/003; G06T 2207/10132; G06T 2207/30168; G06T 2207/10088; G06T 7/0016; G06T 7/70; G06T 11/003; G06T 2207/30032; G06T 2207/30101; G06T 7/174; G06T 7/162; G06T 7/337; G06T 7/60; G06T 7/37; G06T 2207/20128; G06T 2207/20072; G06T 2207/30204; G06T 19/00; G06T 3/4038; G06T 7/30; G06T 7/40; G06T 2210/41; G06T 2207/30024; G06T 2207/10056; G06T 2207/20221; G06T 7/12; G06T 2207/30048; G06T 2207/30008; G06T 11/005; G06N 3/08; G06N 3/04; G06N 3/0454; G06N 7/005; G06N 3/02; G06N 20/00; G06N 3/0445; G06N 3/084; A61N 5/1049; A61N 2005/1061; A61N 5/1067; A61N 5/107; G06K 9/6256; G06V 2201/031; G06V 10/751
USPC ............................................. 378/4, 5, 19, 62
See application file for complete search history.

(56) References Cited

U.S. PATENT DOCUMENTS

| | | | |
|---|---|---|---|
| 10,872,401 B2* | 12/2020 | Schmidt | ................. A61B 6/469 |
| 2004/0101104 A1* | 5/2004 | Avinash | ................. A61B 6/482 |
| | | | 378/98.12 |
| 2007/0263769 A1* | 11/2007 | Roell | ................... A61N 5/1038 |
| | | | 378/65 |
| 2008/0292168 A1* | 11/2008 | Winkelmann | ......... G16H 30/20 |
| | | | 382/238 |
| 2014/0270052 A1 | 9/2014 | Vestevich | |
| 2016/0157800 A1* | 6/2016 | Goyal | .................... A61B 6/486 |
| | | | 600/431 |
| 2019/0038239 A1* | 2/2019 | Flohr | ................... A61B 8/5223 |
| 2019/0046148 A1* | 2/2019 | Suehling | .................. G06N 3/08 |
| 2021/0030301 A1* | 2/2021 | Wang | ................. G01R 33/5601 |

OTHER PUBLICATIONS

Jiang, F. et al: "Artificial Intelligence in healthcare: past, present and future"; In: Stroke and Vascular Neurology; vol. 2; 2017; pp. 230-243; DOI:10.1136/svn-2017-000101.

* cited by examiner

FIG 3

METHOD AND DEVICE FOR COMPUTED TOMOGRAPHY IMAGING

PRIORITY STATEMENT

The present application hereby claims priority under 35 U.S.C. § 119 to German patent application number DE 102019210473.8 filed Jul. 16, 2019, the entire contents of which are hereby incorporated herein by reference.

FIELD

Embodiments of the invention generally relate to a method and to a device for computed tomography imaging, in particular a method for identification of different tissue components and their quantitative evaluation using a combination of multispectral (photon counting) data recording with an iterative data reconstruction and artificial intelligence, in particular using the example of cerebral ischemia in order to predict the use of different therapeutic approaches. The invention is used for imaging, and this way that it can be applied directly within the framework of image reconstruction, can be used for processing reconstructed images, or can generate additional data apart from or as the raw data set in preparation for reconstruction.

BACKGROUND

To date it has not been possible to satisfactorily represent all regions of the human body with an appropriate measuring time for all possible medical indications. For example, in the case of an ischemic stroke, the time, which has elapsed since the occurrence of the stroke, continues to be a criterion for the decision on therapy since a more accurate examination by way of imaging cannot be effectively achieved.

In a time window up to 4.5 hours after the occurrence of an ischemic stroke and damage to the brain tissue, which does not exceed a certain size, the intravenous administration of a drug (r-tPA), which is intended to dissolve the vascular occlusion (clot), is indicated. Since the successful conclusion of different studies on mechanical reopening of the large vessels (mechanical thrombectomy) in 2014, this type of therapy is likewise permitted up to six hours after the occurrence of the vascular occlusion. More recent studies on mechanical thrombectomy have shown that the mechanical reopening of the vessels in a particular subgroup of patients is also promising up to 24 hours after the occurrence of the infarct, however. Criteria for this are the occlusion of a large artery of the brain and the detection of what are known as "tissues at risk", in other words of brain tissue with a reduced blood supply, which is threatened with dying off. At the same time, the volume of the infarct core, in other words, of the irreversibly damaged brain tissue must not be disproportionately large compared to the "tissue at risk". Following on from this, more recent studies disclose the presumption that a medicinal treatment of the vascular occlusion could be promising even beyond the 4.5 hour window. This relates in particular to the group of patients that are known as "slow progressors", in other words the patients in whom the volume of the brain tissue that has died off increases only slowly over the course of time since there is a residual perfusion over what are known as collateral vessels. Current studies are currently examining the use of perfusion imaging for patient selection, but do not consider any further pathophysiological parameters.

Hemorrhaging into the infarct core represents a significant risk to the patient during a treatment, in particular in the case of medicinal lysis therapy, however. This is as a result of the fact that the vessel wall in areas with a reduced blood supply is fragile since the cells die off owing to the reduced oxygen supply and lose their power of adhesion. Proteolytic enzymes, which are liberated when the cell dies, intensify this effect. As a consequence, the vessel wall can no longer withstand the high blood pressure which sets in after the treatment for re-perfusion. The risk of this increases over time. An algorithm would therefore be desirable as a decision-making aid, which allows a statement as to whether the vessel wall is already fragile or is tending to fragility. Therefore, it would be possible to determine the integrity of the vessel wall and identify an elevated risk of bleeding in good time. The latter represents, for example, a contraindication for intravenous lysis therapy after 4.5 hours. In this connection the representation of changes in the vessel wall, which exhibits edema, breaks or hemorrhages, and the analysis and quantification of different tissue components can contribute to decision making.

A further decision-making criterion is the development of the brain edema and its spread characteristics in the area with reduced blood supply. Due to the different localization of the ischemic area and the different distribution of the white and gray matter associated therewith, the spread of the brain edema is not always equal. For this reason, a comparability and statement for an individual patient is difficult.

In addition to detection of the occlusion of a large artery supplying the brain as the basis for a mechanical thrombectomy, an estimation of the success of a treatment is currently made solely by way of the detection of some parameters. These parameters are what are known as the "tissue at risk" or penumbra (reduced blood supply to the tissue without cell death being induced), the infarct core and the brain tissue with a regular blood supply. Only if there is a sufficiently large amount of tissue, which has a reduced blood supply but after restoration of the blood supply is normally supplied and at the same time there is a sufficiently small infarct core, is a treatment, either in the form of a medicinal lysis therapy or a mechanical thrombectomy indicated. Due to the increasing risk of a hemorrhage in the infarct core over the course of time, an "onset to treatment time" of more than 4.5 hours for the intravenous lysis therapy with r-tPA is currently the limiting factor. Therefore, intravenous lysis therapy is withheld from a not inconsiderable number of patients, in part also with what is known as a "Wake Up" stroke, within the time window, although in individual cases treatment was successful even beyond the time window of 4.5 hours.

Further information on the integrity of the vessel wall is not currently available. Therefore, it is not possible to reliably predict whether the patient will experience a hemorrhage in the infarct area if the lysis therapy occurs beyond the 4.5 hour window. Earlier studies have shown that in this case there is a higher risk of bleeding.

This example is representative of medical incidences in which, currently, imaging is not possible or is possible to only a limited extent, and nevertheless parameters have to be derived from clinical images in order to define an optimum therapy.

SUMMARY

Embodiments of the present invention provide a method and a device for computed tomography imaging, in particular a method and a device for controlling a computed tomography system or a diagnosis system with which the drawbacks of the prior art are overcome and improved imaging is achieved in respect of an improved possibility of tissue characterization. In particular, an object of the invention is to separate (basically all) tissue structures with low differences in density, preferably tissue structures in the brain tissue.

Embodiments are directed to a method, a device, a control device, a diagnosis system and a computed tomography system.

The inventive method of at least one embodiment relates to an improvement in CT imaging and serves to better distinguish between different tissue types of an object. In particular, diseases which are accompanied by a change in the water content (edema formation) in regions having different tissue types which are very close together can be identified. The disease can spread to both tissue types and have different therapeutic or diagnostic relevance, for example in the case of tumor diseases or fractures.

An inventive method of an embodiment, for computed tomography imaging or for controlling a computed tomography system or a diagnosis system, comprises:

provision of a CT data set of an object;

suppressing a contrast, which has been caused by (at least) one tissue type, preferably by contrasts, which have been caused by two different tissue types, and generating a contrast-suppressed data set; and analysis of at least the contrast-suppressed data set or a data set based on the contrast-suppressed data set;

The inventive device of at least one embodiment, for computed tomography imaging or for controlling a computed tomography system or a diagnosis system, which is configured particularly preferably to carry out an inventive method, comprises:

a data interface configured to receive a CT data set of an object, wherein the CT data set has been recorded by way of a multispectral recording method, optionally, a data interface configured to receive a comparison data set of an object, wherein the comparison data set has been recorded by way of the multispectral recording method. This can be the same data interface as stated above.

a contrast suppression unit is configured for suppressing a contrast, which has been caused by one tissue type (or by two or more different tissue types), and generation of a contrast-suppressed data set, and an analysis unit configured for analysis at least of the contrast-suppressed data set or a data set based on the contrast-suppressed data set (for example the resulting data set mentioned further below) by way of a machine learning algorithm, wherein the analysis is configured to identify at least one change in the tissue type (or of two or more different tissue types).

In an embodiment, an inventive control device for controlling a computed tomography system or a diagnosis system is configured for carrying out an embodiment of an inventive method and/or comprises an embodiment of an inventive device.

In this regard, an embodiment is also directed to a corresponding computer program product having a computer program, which can be loaded directly into a computer system (in order to create a device) or a storage device of a control device of a diagnosis or computed tomography system, having program segments in order to carry out all steps of of an embodiment the inventive method when the program is run in the computer system or control device. In addition to the computer program, a computer program product of this kind can optionally comprise additional components, such as documentation and/or additional components, also hardware components, such as hardware keys (dongles, etc.), in order to utilize the software.

In this regard, an embodiment is also directed to a computer-readable medium, for example a memory stick, a hard disk or another portable or permanently fitted data carrier, on which the program segments of the computer program, which can be read in and executed by a computer system or an arithmetic unit of the control device are stored, can be used for transportation to the computer system or control device and/or for storage on or in the computer system or control device. The arithmetic unit can have, for example, one or more cooperating microprocessor(s) or the like for this purpose.

At least one embodiment is directed to a method for computed tomography imaging, comprising:

provisioning a CT data set of an object, the CT data set being previously recorded via a multispectral recording method;

suppressing a contrast, caused by a tissue type, and generating a contrast-suppressed data set from the CT data set provisioned; and analyzing at least the contrast-suppressed data set generated or a data set generated via a machine learning algorithm based on the contrast-suppressed data set, the analyzing being configured to identify at least one change in the tissue type.

At least one embodiment is directed to a device for computed tomography imaging, comprising:

a data interface, configured to receive a CT data set of an object, the CT data set being previously recorded via a multispectral recording method;

a contrast suppression unit configured to suppress a contrast caused by a tissue type, and configured to generate a contrast-suppressed data set;

an analysis unit configured to analyze, via a machine learning algorithm, at least one of the contrast-suppressed data set or a data set based on the contrast-suppressed data set, the analyzing being configured to identify at least one change within the tissue type.

At least one embodiment is directed to a control device for controlling a computed tomography system or a diagnosis system, comprising:

the device of an embodiment.

At least one embodiment is directed to a diagnosis system comprising:

the control device of an embodiment.

At least one embodiment is directed to a computed tomography system, configured to record a CT data set via a multispectral recording method, comprising:

the control device of an embodiment.

At least one embodiment is directed to a non-transitory computer program product storing a computer program, directly loadable into a storage device of a control device, the computer program including program segments to carry out the method of an embodiment when the computer program is run in the control device.

At least one embodiment is directed to a non-transitory computer-readable medium storing program segments, readable and executable by an arithmetic unit, to carry out the method of an embodiment when the program segments are executed by the arithmetic unit.

BRIEF DESCRIPTION OF THE DRAWINGS

The invention will be explained again in more detail below with reference to the accompanying figures using example embodiments. Identical components are provided with identical reference numerals in the different figures. As a rule, the figures are not to scale. In the drawings.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The inventive method of at least one embodiment relates to an improvement in CT imaging and serves to better distinguish between different tissue types of an object. In particular, diseases which are accompanied by a change in the water content (edema formation) in regions having different tissue types which are very close together can be identified. The disease can spread to both tissue types and have different therapeutic or diagnostic relevance, for example in the case of tumor diseases or fractures.

The object can be an inanimate element but is preferably part of a patient (human or animal). The examined object can be comprehended as a particular region, for example a region or an organ in a body, which is often also called the Region of Interest (RoI). The tissue features of interest (also called "compartments", for example the consistency of the white or gray matter or the liver consistency) are to be understood in respect of the types of tissue (or "tissue types", for example gray and white brain matter) to be differentiated. Often these are the water and fat content. In some cases, Region of Interest and tissue type (compartment) can be identical, for example in the brain ventricle system.

An inventive method of an embodiment, for computed tomography imaging or for controlling a computed tomography system or a diagnosis system, comprises:

provision of a CT data set of an object, wherein the CT data set has been recorded by w of a multispectral recording method, for example via a dual or multispectral recording method, in particular Dual Source Dual Energy method or Multi/Dual Source Multi Energy method, particularly preferably by way of a photon counting method. The computed tomography data set comprises raw data or (reconstructed) image data of an object to be examined. Possibilities for a multispectral recording method are known to the person skilled in the art. It should be taken into consideration, however, that the resolution is sufficient spectrally and spatially as well as the dose efficiency.

A data set can be provided by way of a Radiology Information system (RIS), wherein the data set can have been recorded directly or can be retrieved from a PACS (Picture Archiving and Communication System).

The inventive method of an embodiment, for computed tomography imaging or for controlling a computed tomography system or a diagnosis system, further comprises suppressing a contrast, which has been caused by (at least) one tissue type, preferably by contrasts, which have been caused by two different tissue types, and generating a contrast-suppressed data set. For example, in an examination of the brain, the gray-white contrast is suppressed, in other words, the contrast of the gray brain matter and the white brain matter. For an optimum representation, the contrasts of all known and healthy tissue types present in a RoI should actually be suppressed. This is not imperative, however, since known tissue types could also be rendered identifiable by a corresponding marking (and then be ignored during the subsequent analysis). It is important, however, that the image signals of the healthy tissue in which the relevant examination is to be performed should be suppressed.

As a result of the contrast suppression, a change (for example an edema) within the examined tissue regions can be visualized since the image information of the healthy tissue is faded out. Even if the processing of (reconstructed) image data is preferred in this framework, this step can also still occur within a pre-processing of the raw data before the image reconstruction. When applied to different regions of the body it is frequently necessary to suppress different contrasts. Two, three or more tissue types can form the basis of the contrast suppression instead of just one. The contrast suppression supplies advantageous contrast information, which reflects the change in tissue types, for example the edema content (severity and affected areas) in the data set.

Often a pathology is overlaid by a contrast and "hidden" by it. For example, an edema (water) in the brain tissue can be identified only with difficulty since the gray-white contrast overlays the water/brain contrast and consequently the latter can be identified only with difficulty. In addition, the edema characteristic is different in gray and white matter and has different diagnostic relevance. Generally, in relation to contrast suppression within the meaning of the invention, it can be stated that in the case of an examination of tissue types, the contrast, which is characteristic of the respective tissue types, but not of the change (to be examined) in a tissue type, is suppressed.

The contrast suppression should preferably be based on the energy-dependent attenuation of radiation through different materials, and therewith render these materials differentiable owing to their energy-dependent attenuation. This allows, for example, gray matter and white matter to be differentiated and the water content to be visualized. For this purpose, it is preferable to differentiate different tissue types (for example differentiate gray matter from white matter), and this will be explained in more detail below within the framework of iterative data processing.

If this method is applied to different objects and pathologies (for example different regions of a human body), the Hounsfield values of the respective tissue types should preferably be taken into account for contrast suppression. With tumors in the brain, for example the same parameters are applicable; with tumors of the liver, regional specific thresholds must be taken into account, however. For example, the gray and white matter in the brain have energy-specific properties, which can be used within the framework of the contrast suppression. These properties are used to enhance or weaken selective information from the corresponding raw data or image data (for example voxels from 3D images). Consequently, for example information about the water content that is "hidden" in the gray/white noise becomes visible for the first time due to the contrast suppression. Generally, it is preferred therefore that the contrast suppression is based on the contrast between two (or more) different attenuations of the energy.

The inventive method of an embodiment, for computed tomography imaging or for controlling a computed tomography system or a diagnosis system, further comprises analysis of at least the contrast-suppressed data set or a data set based on the contrast-suppressed data set (for example of the resulting data set mentioned below) by way of a machine learning algorithm, with the analysis being configured to identify at least one change of the tissue type (or of two or more different tissue types). A machine learning algorithm is an algorithm based on the principle of machine learning, which is sometimes also called "artificial intelligence". The English name is frequently used in German, however.

The analysis is preferably configured such that it can make statements about the probability of the occurrence or course of a predetermined pathology due to the change, for example the probability of a hemorrhage in brain tissue. Alternatively or in addition, the analysis is preferably configured such that it allows statements about the probability of a response to different therapy options and/or about a clinical prognosis. The method can thereby contribute to therapy decisions, and this advantageously entails an increase in diagnosis and treatment safety. This helps to reduce complications and make the treatment more cost-effective.

In general, the analysis is configured such that it determines properties of those regions which are highlighted after the contrast suppression. Not necessarily all regions that are still visible are meant thereby, however (for example cranial bone in an examination of the brain tissue), but primarily those regions, which are to be examined as intended, in other words should actually have a different tissue property. The relevant properties are for example the shape of the relevant regions, the size, the properties (for example the Hounsfield Units) or the position. Before the analysis it is preferable to define those regions, which are to be examined or, in addition, to eliminate from the CT data set the image information of tissue types, which are not to be examined, for example likewise by contrast suppression, or at least to identify them, for example by marking or masking. The analysis can of course also use the original CT data set or data sets derived therefrom.

Preferably, hemorrhages, swellings and changes in the tissue structure are taken into account in an analysis of the structure and character of a vessel wall. An important item of information obtained from this information is the statement about the probability of a vessel rupture after restoration of the circulation. Therefore, for example the probability of a life-threatening hemorrhage, in particular in brain tissue, can be determined. This also helps to make a diagnosis and a therapy, in particular in the case of a stroke, more reliable.

A system for the artificial generation of knowledge from experience can be called a method of "machine learning" or an artificial intelligence system. Machine learning denotes here a collection of mathematical methods of pattern recognition. These methods enable pattern recognition, for example by way of best-possible deconstruction of databases into hierarchical structures (decision trees), or determining similarities between data sets by way of vectors (for example k-nearest neighbor) et al.

What is known as deep-learning machine learning using artificial neural networks designates a special form of machine learning. Instead of the term "neural network", the term "neural network" can also be used. In particular, a trained function can also be a deep artificial neural network (deep neural network) and/or a convolutional neural network (CNN). The artificial neural network used here is constructed similar to a nervous system, with the neurons being networked with each other. The first layer of the neural network, the input layer, processes an input data input, such as image parameters (for example a gray scale value) of an individual pixel or voxel or a group of pixels or voxels of an image or an image data set. This first layer forwards its outputs to the next layer. This second layer processes the information of the preceding layer and likewise passes on the result. The next layer receives the information from the second layer and processes it further. These layers are called hidden layers. The features contained in them are increasingly abstract. The result is output in the output layer. In order to "learn" the processing of the input data, the artificial neural network is trained using training data sets. Corresponding methods (for example Supervised Learning, Unsupervised Learning, Reinforcement Learning) are known to the person skilled in the art.

If the aim of the method is to determine the probability of a hemorrhage (for example in brain tissue in the case of a stroke), in particular with administration of a drug, the relevant machine learning algorithm was trained by way of training data sets, which were selected in respect of the prediction of the probability of hemorrhage, in particular after administration of the relevant drug (for example r-tPA). Alternatively or in addition, however, training data sets from other therapy approaches and/or a prediction of the clinical progress made by a physician can be used.

In the case of a stroke, according to present knowledge, the water/edema content or its change seems to be significant for the probability of hemorrhage. For this reason, firstly the water content in different compartments is highlighted by the contrast suppression and then determined by the analysis. From the data then obtained the probability of hemorrhaging can likewise be determined and a decision on therapy made within the framework of the analysis, supported by artificial intelligence.

The data sets can be evaluated with artificial intelligence ("AI", the machine learning algorithm) correspondingly trained on raw data or image data and be compared, for example with a patient collective, with the data of the patient collective having been used for training the algorithm. With this patient collective, the clinical progress and/or the results of imaging should be known for this. For example, a pattern comparison of the current patient in respect of edema characteristic, the quantification of different tissue components and/or properties of the vessel wall with the underlying patient collective permits a statement about the probability of hemorrhaging but also about the clinical result. As a function of this a treating physician can then supply the indication for an appropriate therapy.

One advantage of the method is that, with the aid of this imaging technology, a higher spatial resolution can be achieved as the basis of improved image evaluation. On this basis and based on the information about the material properties, as is enabled particularly well by the technology of photon counting, for example the distribution of water in a tissue (edema) and the consistency and properties of a vessel wall (for example in respect of a hemorrhage), a fat or calcium content, an inflammation, a porosity, etc. can be determined more accurately. In addition, the individual components of the tissue can be quantified and used for decision-making therefore. Furthermore, it is possible to characterize and visualize different tissue types (in particular by way of the information obtained by the contrast suppression). In connection with the analysis, changes, for example spreading pattern of an edema in the brain tissue (with differentiated consideration of the white and gray matter, which exhibit a different dispersion characteristic) can then be analyzed and, be analyzed in comparison with a patient collective for which distribution patterns but also clinical progressions are known.

A quantification of results is preferably made via the combination of two values, namely the spatial extent and the tissue property, with the latter being characterized by the HU distribution (HU: Hounsfield Unit). Contrast suppression of the tissue structure consequently leads to the potential to standardize the changes. The quantification makes comparison with a control group and consequently the determination of the probability possible.

As will be stated in more detail in the following, for the method a multispectral photon counting recording method is preferably combined with an iterative data reconstruction and, in particular, a simultaneous phantom measurement. Using this particular combination an expanded analysis of some pathologies is possible, in particular optimum separation of white and gray brain matter.

In photon counting computed tomography (photon-counting CT) individual photons, which strike a pixel detector are counted. A photon-counting CT system uses a photon-counting detector (PCD), whose detector pixels can register and count individual photons. In addition, photons within pre-adjustable energy bins can be counted. The individual detector pixels thereby assume an energy spectrum, and this ultimately produces a spectral or energy-resolved image recording. In contrast thereto, conventional CT scanners are based on an energy-integrating recording technique, in which the total energy (in general of a large number of photons and electronic noise), which is measured integrated in a pixel during a fixed time frame. Therefore, conventional CT scanners only have to measure the photon intensity, comparable with black and white photography, whereas with photon-counting CT, spectral information is also registered, similar to color photography. A particular advantage of photon counting CT is a very low noise component.

Preferably provided as a final step is displaying of the data on a display device, for example a screen. Preferably, different compartments, in other words regions, in which different tissue features have been identified during processing, are displayed in different ways, for example using different colors or a different texture. A representation of the information as a color superimposed edema content on the gray-white images of a CT scan of the brain is conceivable. In respect of the evaluation of the edema, this superimposition advantageously provides essential information since the significance of the edema in the two substances is considerably different. A visual representation using a 3D model of the object (for example of the individual brain tissue) and its regions (for example gray and white matter) is also preferred. As stated above, the essential information can be visualized so as to be color coded and optionally also superimposed.

The inventive device of at least one embodiment, for computed tomography imaging or for controlling a computed tomography system or a diagnosis system, which is configured particularly preferably to carry out an inventive method, comprises:

a data interface configured to receive a CT data set of an object, wherein the CT data set has been recorded by way of a multispectral recording method, optionally, a data interface configured to receive a comparison data set of an object, wherein the comparison data set has been recorded by way of the multispectral recording method. This can be the same data interface as stated above.

a contrast suppression unit is configured for suppressing a contrast, which has been caused by one tissue type (or by two or more different tissue types), and generation of a contrast-suppressed data set, and an analysis unit configured for analysis at least of the contrast-suppressed data set or a data set based on the contrast-suppressed data set (for example the resulting data set mentioned further below) by way of a machine learning algorithm, wherein the analysis is configured to identify at least one change in the tissue type (or of two or more different tissue types).

Reference is made to the fact that embodiments of the invention does not primarily serve to represent information, but predominantly to process CT data sets. This processing is not trivial and cannot be simply carried out by way of calculations by a human, and, as a rule, in all iterative data processing methods within the framework of image processing. By way of the invention it is possible to carry out both a qualitative and a quantitative analysis of tissue.

In an embodiment, an inventive control device for controlling a computed tomography system or a diagnosis system is configured for carrying out an embodiment of an inventive method and/or comprises an embodiment of an inventive device.

In an embodiment, the inventive device for computed tomography imaging can, however, also be designed per se as a device for controlling a CT system. Alternatively or in addition, an embodiment of the inventive device for computed tomography imaging can be designed as a device for controlling a diagnosis system.

In an embodiment, the inventive device can also be connected to a CT device, for example in particular over a network. The device can also be designed in an alternative design as part of a CT device. In particular, individual modules or components of the device can also be arranged in a network or be functionally connected over a network.

A network can be a local network (Local Area Network, "LAN" for short) or a Wide Area Network ("WAN" for short). An example of a local area network is an intranet, an example of a wide area network is the Internet. The network can in particular also be designed to be wireless, in particular as a WLAN (for "wireless LAN", the abbreviation "WiFi" is common in English) or as a Bluetooth connection. The network can also be designed as a combination of the examples.

An inventive computed tomography system of an embodiment is configured for recording a CT data set by way of a multispectral recording method, with a photon counting computed tomography system being preferred, comprises of an embodiment an inventive control device.

An inventive diagnosis system of an embodiment comprises an inventive control device. The method described above is particularly advantageous when used in a corresponding diagnosis system. Therefore the diagnosis system can alternatively be configured for carrying out of an embodiment an inventive method. The diagnosis system can be an independent system, which can access, for example, a PACS or it can be integrated directly in a CT system (for example a CT scanner). It is also preferred that there is an interactive data communication between CT system and diagnosis system, in particular to be able to optimally implement computing-intensive steps of the raw data preparation (for example, flexible binning).

A diagnosis system is a system or an arrangement, enabling the analysis and/or processing of data, which was acquired or recorded with a CT system (what is known as CT data). Analysis and/or processing of CT data or CT data sets can comprise, in particular, the reconstruction of image data from raw data, the secondary processing of image data or raw data, the analysis of image data or raw data, the segmenting of structures in image data, the identification or quantification of anatomical structures, in particular of pathologically changed anatomical structures in image data, and similar steps of image and data processing.

Even if within the framework of the description fat and water or gray and white matter are frequently mentioned as examples, other materials such as calcium, iodine, blood, cholesterol, fat, iron, etc. can be differentiated and changes determined as well using the invention. All possible tissue types can be examined using the invention on the basis of the differentiability of materials (for example the substances) in respect of the contrasts (differentiated, characterized, and quantified). For example, a clot in the vessel, or a fragile vessel wall can be identified.

The majority of the components of the device or the control device can be wholly or partially implemented in the form of software modules in a processor of a corresponding device or control device. An implementation largely in terms of software has the advantage that even previously used control devices can be easily retrofitted by way of a software update in order to operate inventively.

In this regard, an embodiment is also directed to a corresponding computer program product having a computer program, which can be loaded directly into a computer system (in order to create a device) or a storage device of a control device of a diagnosis or computed tomography system, having program segments in order to carry out all steps of of an embodiment the inventive method when the program is run in the computer system or control device. In addition to the computer program, a computer program product of this kind can optionally comprise additional components, such as documentation and/or additional components, also hardware components, such as hardware keys (dongles, etc.), in order to utilize the software.

In this regard, an embodiment is also directed to a computer-readable medium, for example a memory stick, a hard disk or another portable or permanently fitted data carrier, on which the program segments of the computer program, which can be read in and executed by a computer system or an arithmetic unit of the control device are stored, can be used for transportation to the computer system or control device and/or for storage on or in the computer system or control device. The arithmetic unit can have, for example, one or more cooperating microprocessor(s) or the like for this purpose.

Further, particularly advantageous embodiments and developments of the invention can be found in the dependent claims and the following description, wherein the claims of one category can also be developed analogously to the claims and descriptive parts relating to a different claim category and in particular individual features of different example embodiments or variants can be combined to form new example embodiments or variants as well.

According to a preferred method, the provision of the CT data set of the object comprises recording within the framework of a multispectral recording method, with a multispectral resolving detector, preferably a photon-counting detector, being used for recording the provided CT data set.

A detector is preferably used which allows flexible binning. Flexible binning way that it is possible to optimize the spectral data or a reduction in the measuring accuracy can be achieved. Flexible binning is known to the person skilled in the art. Binning is taken to mean classification of measured values during data taking or data processing. The target quantities of the measured values are divided into intervals in ascending order of size, into what are known as bins. The measured values are then replaced by those representatives of the interval in which the measured values are located. In the case of flexible binning, the bin widths, in other words the size of the intervals, can (optionally individually) change.

According to a preferred method, during analysis, the position of an area (for example a brain region) with a change within the tissue types (for example an edema in the gray and white matter) examined there or its size or severity or a characteristic of the change (for example a characteristic of the edema) is also determined. Furthermore, a prediction of a clinical result and/or a possible treatment is preferably determined. This advantageously serves to assist with decisions on therapy strategy. During the course of an examination it is also preferred to determine the degree of progress during a follow-up examination.

According to a preferred method, the analysis is made by way of a machine learning algorithm based on models of the following group: Markov models, neural networks, convolution algorithms and 3D lattice models, in particular on the basis of a 3D reconstruction of image data.

A preferred method comprises the following additional steps:

provision of a comparison data set (in particular based on a phantom), with the comparison data set having been recorded by way of the multispectral recording method. The comparison data set therefore comprises data, which can be compared directly with the CT data set since in each case the identical (in particular the same) recording method was applied.

The comparison data set comprises data relating to the anticipated tissue types, in particular also the tissue types changed by the pathologies. The comparison data set preferably comprises CT data of a standardized phantom with defined tissue types to be measured as intended in the object, for example the tissue types of different brain compartments (for example gray and white brain matter), and, as a function of the problem and the expected pathology, also comparison data sets in this regard. In principle, the method can also be carried out with comparison data sets, however, which are not based on a phantom, for example the comparison data set can comprise scanner-specific calibration curves.

A comparison data set can be provided by way of an RIS, wherein the comparison data set can be recorded directly or can be retrieved from a PACS.

processing one of the data sets by way of an iterative data reconstruction, with an optimization of the relevant data set being performed on the basis of the comparison data set. With iterative data processing a known reference, forming the basis of a comparison data set, can be reconstructed until the reference is satisfactorily represented, and then the corresponding reconstruction steps are applied to the relevant data set.

An iterative data reconstruction uses iterative algorithms to reconstruct 2D and 3D images. In computed tomography, as a rule an image has to be reconstructed from projections of an object. Iterative reconstruction techniques represent a better, but more computing-intensive, alternative to conventional Filtered-Back-Projection methods (FBP) with which the image is calculated directly in a single reconstruction step. However, there are possibilities for achieving extremely fast calculations and great parallelism for the iterative reconstruction, and this renders the iterative reconstruction practical for commercialization. The reconstruction of an image from the acquired data is an inverse problem. Often it is not possible to directly solve the inverse problem exactly. In this case a direct algorithm has to approximate the solution, and this can lead to visible reconstruction artifacts in the image. Iterative algorithms approximate the correct solution with a plurality of iteration steps, whereby it is possible to achieve a better reconstruction at the cost of a higher computing time.

There is a large number of algorithms, which in each case begin with an assumed image (the image is here the known reference on which the comparison data set is based), however, calculate projections from the image, compare the original projection data and update the image on the basis of the difference between the calculated and the actual projection. Preferred algorithms are algorithms for algebraic reconstruction, for iterative Sparse Asymptotic Minimum Variance (SAMV), for statistical reconstruction and for learned iterative reconstruction. The algebraic reconstruction technique (ART) was the first iterative reconstruction technique, which was used by Hounsfield for the computed tomography. An iterative Sparse Asymptotic Minimum Variance algorithm is an iterative, parameter-free, high-resolution tomographic reconstruction method, which is inspired by compressed sensing. With learned iterative reconstruction, the updating algorithm is learned from training data using techniques of machine learning such as neural convolution networks, while the image formation model continues to be included. As a rule, this leads to faster and higher quality reconstructions.

Iterative data processing achieves an optimum selection of the best data points, which were obtained from the multispectral imaging and enables an optimized representation of a selected compartment (a region having the same tissue type, for example gray matter). This occurs by way of an optimization of the signal behavior of the object that is to be expected on the basis of a priori knowledge in the comparison data.

The comparison data set is iteratively processed in a convoluted manner, with, preferably in each case, the differentiability of the references to the individual tissue types being checked and a quantitative differentiating factor being associated with this differentiability. This differentiating factor is then maximized to achieve an optimum differentiability. Parallel to this, the same parameters for data processing are applied to the CT data set and, in particular, a further differentiating value is associated with the results (for example by manually marking representative tissue regions).

The iterative approach forms an advantageous algorithm for optimum selection of the best data points, which were obtained from the multispectral imaging and enables an optimized representation of a selected compartment (for example gray matter). This occurs by way of an optimization of the signal behavior that is to be expected on the basis of a priori knowledge, measured as a comparison data set (for example, since the phantom is known) and measured in the patient. The a priori knowledge increases the accuracy of the reconstruction and therewith the reliability of the results.

After recording of the CT data set (as raw data or as reconstructed image data), the iterative data processing (optionally as image reconstruction) can be applied to this data set. Alternatively or in addition, the iterative data processing can be applied to the contrast suppression (for example to improve a gray-white suppression) and/or the contrast-suppressed data set and/or the resulting data set (for example to improve the edema representation). In particular, iterative data processing occurs within the framework of the analysis, with machine learning algorithms being inventively involved in iterative data processing in this case.

Iterative reconstruction is very advantageous but not imperative, it can prepare the data sets better in the case of analysis or for the analysis and thereby improve or even make possible for the first time a qualitative or quantitative evaluation. For example, the distinction between gray and white matter can be improved even further by way of iterative methods. In particular, data sets can be better prepared for (or during the) analysis by way of iterative reconstruction and a qualitative or quantitative evaluation improved as a result.

The comparison data set is preferably the CT data set of a phantom, which comprises samples, which match the tissues to be examined on the object, in other words the different tissue types, which are present in the compartments. The provision of the comparison data set comprises recording the phantom within the framework of the multispectral recording method, with the phantom preferably being recorded at the same time as (simultaneously therefore) the object is recorded.

The phantom is preferably fixed to the device (for example to the headrest) or, depending on the type of examination, it is preferably modularly attached to other structures or to the patient and introduced into the examination procedure. A machine-learnable identification of this phantom is also preferred for simplification of the automated evaluation including quality control. A simultaneous measurement together with a phantom is used to improve the result and to rule out variations between different scanners (for example variances in the measuring accuracy or comparability between different devices) or the standardization of the measuring results. A simultaneous measurement has the advantage that individual variations of the scan, for example artifacts, can display acentric support better.

A preferred method comprises the additional step of provision of a database, containing further comparison data sets relating to different tissue types and preferably also to pathologies. This database can also be called an "atlas" and preferably comprises data relating to an anatomical and/or pathological signal behavior and, in particular, variations in signal behavior. The database preferably comprises comparison data sets of tissue types of different body regions or compartments. The comparison data sets present in the database have preferably been created with the inventive method and therefore contain information about relevant aberrations. The atlas advantageously helps to increase the accuracy of the evaluation.

This database is preferably integrated in an algorithm for data evaluation. This database is used particularly preferably for training the machine learning algorithm (a machine learning algorithm used in analysis and/or a machine learning algorithm used within the framework of iterative data reconstruction).

As already indicated above, iterative data reconstruction preferably comprises an algorithm based on a principle of machine learning, preferably a deep learning algorithm, with a comparative evaluation of different regions of the object preferably occurring, particularly preferably a side-comparing evaluation. With a side-comparing evaluation, different sides of the object are compared with each other, for example if the object is a brain, the two brain halves. Symmetries between the two sides is used here to determine one of the sides.

During processing a multivariable solution can occur, depending on the number of compartments to be examined (for example optimized data sets for gray or white matter, calcification, hemorrhages, etc.) and generating new data sets by using an iterative approach to the improved representation of a desired feature. The use of deep learning is very advantageous for optimum processing of the volume of data resulting therefrom.

In the framework of a machine learning approach a device is preferred in which the processing unit comprises a number of machine learning algorithms, preferably two or more machine learning algorithms, which, functionally interlaced with each other, carry out data processing.

In the case of iterative data reconstruction there is preferably a combination of two or more different evaluation algorithms, which functionally interconnect. The algorithms preferably induce different types of data processing and are connected together particularly preferably by way of a quantitative distinguishing factor.

According to a preferred method, within the framework of suppressing the contrast, the relevant contrast is suppressed to more than 50%, preferably to more than 75% (or even 90%), particularly preferably to 100%. Since, in particular image data is being worked with, which simplifies a concluding examination by a physician, the contrast-suppressed data set preferably comprises reconstructed image data with suppressed contrast.

According to a preferred method, image data is reconstructed from the data sets during or before the analysis, with image data preferably being reconstructed from the CT data set. The subsequent steps of the method, in other words the contrast suppression and/or the analysis are preferably no longer carried out with the raw data in this case, but with the reconstructed image data. In the course of reconstruction, three-dimensional image data is particularly preferably reconstructed. This is advantageous since a decision on therapy is often based on volume details. An optional superimposition of the contrast-suppressed data set with the CT data set can preferably occur completely on the basis of the 3D image data in this case, in particular with surface contouring from the 3D image (in other words, the three-dimensional image data).

According to a preferred method, the tissue types are identified on the basis of the CT data set. This preferably occurs by way of iterative data processing as described above. This step preferably occurs before suppression of the contrast or at least before the analysis. The identification is based preferably on the water and/or fat content in the CT data set. For example, after images reconstructed from the CT data set have been analyzed in terms of their water and fat content, an analysis is made using artificial intelligence in order to identify areas affected by a stroke.

Preferably, an identification is made using a database which could here likewise be called an "atlas" since it also contains comparison data sets. Part of the CT data set (which also comprises the complete CT data set) is compared here with this atlas of known data on tissue types, with the atlas preferably comprising variations of CT signals measured for different tissue types (of the object) and for reconstructions of these CT signals, in particular CT signals, which are based on recordings of tissue types changed by a pathology. There is therefore a comparison of the CT data set with data from a database. Variations, which cannot be reliably identified by the knowledgeable experts, can be represented in the specific data set and in the comparison with the large cohort as well here. This applies both to intra- and interindividual variations at a fixed instant or in the interval.

In addition to anatomical information the atlas preferably also comprises information about the behavior of pathologies (for example of an edema) and, connected therewith, information about probabilities of indications (for example the risk of a hemorrhage in the brain), in particular in the form of quantitative details or formulae, which together with results of the analysis provide quantitative details on probabilities.

According to a preferred method, the contrast-suppressed data set and the CT data set (in other words, the data set without contrast suppression) are superimposed to form a resulting data set. In other words, a resulting data set is created, which comprises a superimposition of the CT data set and the contrast-suppressed data set. Labelled data can be superimposed, for example in the case where raw data is being used, or there can be a visual superimposition (if reconstructed image data is being used), for example based on "contour-fit" models. Preferably, images (in particular 3D images) from the CT data set are registered with images from the contrast-suppressed data set. This superimposition allows statements about changes in tissue types, for example the different edema content of the gray and white matter.

For a superimposition, a preferred device comprises a superimposition unit configured for superimposition of the contrast-suppressed data set with the CT data set to form a resulting data set. The superimposition unit can be part of the contrast suppression unit.

A preferred device comprises an identification unit configured for automatic identification of the region in a body in which the CT data set has been recorded. This identification unit can comprise, for example, a body atlas and, by way of comparison of the recorded image data with the body atlas, determines the relevant region. Identified regions are preferably also automatically labeled or a CT data set is given a corresponding label on the basis of this identification. The identification unit can be part of the contrast suppression unit.

According to a preferred method, the CT data set is a multispectral recording of a brain, in particular a brain of a stroke patient. In the course of contrast suppression the gray-white contrast of the gray matter and the white matter is suppressed and the contrast-suppressed data set comprises information based on this suppressing of the gray-white contrast. The analysis is configured to identify at least one change, in particular an edema, within the white matter and/or the gray matter.

A preferred device comprises a data interface configured for controlling a computed tomography system, which is configured to record a CT data set by way of a multispectral recording method, in particular for controlling a dual source dual energy computed tomography system or a multi/dual source multi energy computed tomography system, particularly preferably a computed tomography system, which is configured for measurements based on a photon counting method. The data interface cited here can be the same one via which the device can receive data if the data interface is capable of bidirectional communication.

The method can also comprise elements of "Cloud computing". In "Cloud computing" an IT infrastructure, for example storage space or computing power and/or application software is provided over a network. The applicant and the "Cloud" communicate by way of data interfaces and/or data transfer protocols.

In the framework of "Cloud computing", in a preferred embodiment of the inventive method, data is provided via a data channel (for example a network) to a "Cloud". This "Cloud" comprises a (remote) computer system, for example a computer cluster, which, as a rule, does not comprise the local computer of the user. This Cloud can be provided in particular by the medical institution, which also supplies the medical systems. In particular, the data of the CT data set is sent via an RIS or a PACS to a (remote) computer system (the "Cloud"). Preferably, the computer system of the "Cloud", the network and the relevant CT system represent an interconnection in the linked sense. The method can be implemented in the network by way of a combination of commands. The data or results calculated in the Cloud is/are preferably sent again via a data channel (for example over a network) to the local computer of the user. For example, the data of the provided CT data set is processed by a computer system of a hospital according to the inventive method and the results of this processing are sent back again to the user by an RIS or a PACS.

In the framework of a preferred embodiment of the inventive device, components relevant to the invention are present on the part of the "Cloud". In addition to such a device a preferred system also comprises a local arithmetic unit, which is connected by a data channel (for example a network, in particular configured as an RIS or a PACS) to the device. The local arithmetic unit comprises at least one data receiving interface in order to receive data. In addition it is preferred if the local computer also has a transmit interface to send data to the device.

Advantages of embodiments of the invention are an extension of the clinical use of CT imaging, in particular of the native representation of the brain and other body regions, an improved semi-quantifiable representation of pathological processes (for example an inflammation, an atrophy, an edema or a tumor) and standardization of the diagnosis and therewith achieving a greater diagnostic confidence and the representation of changes in the tissue that could not previously be detected or could only be inadequately detected. A further advantage is the possibility of using CT in patients with contraindications to MRT and faster image data acquisition, in particular in the case of emergency treatment but also with uncooperative patients, and an improvement in the quality control of the CT.

Figure 1:
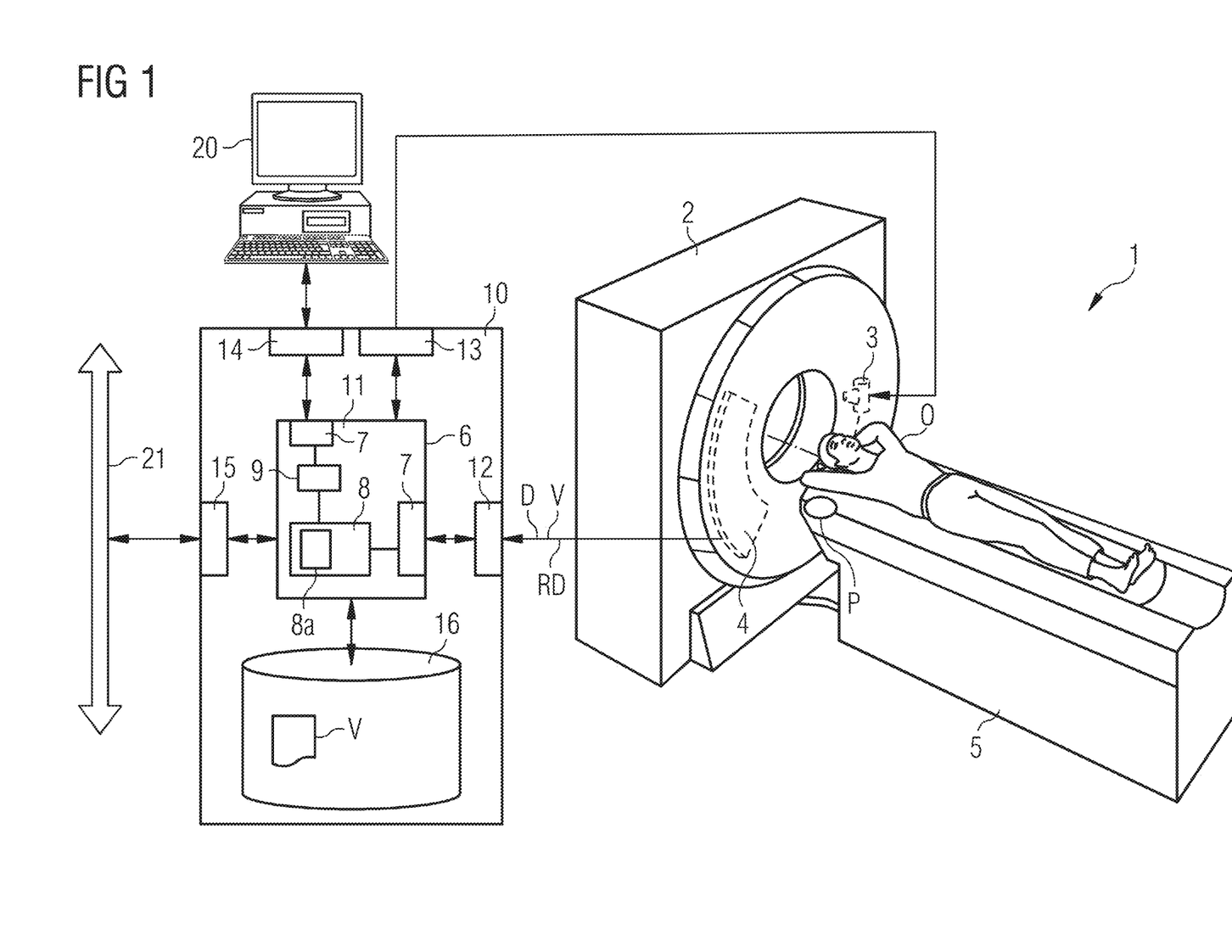
FIG. 1 shows a roughly schematic representation of a computed tomography system with an example embodiment of a control device with an inventive device for carrying out the method.

FIG. 1 shows roughly schematically a computed tomography system 1 with a control device 10 for carrying out the inventive method. The CT system 1 is configured here as a photon-counting system and conventionally has a scanner 2 with a gantry in which an X-ray source 3 rotates, which in each case penetrates a patient, who is pushed into a measuring space of the gantry by way of a couch 5, so the radiation strikes a detector 4, which is a photon-counting detector, opposing the X-ray source 3 in each case. Reference is explicitly made to the fact that the example embodiment of FIG. 5 is only one example of a CT and the invention can also be used on any multispectral recording CT constructions, for example with annularly fixed X-ray detector and/or a plurality of X-ray sources.

Similarly, with the control device 10 only the components which are essential to the explanation of the invention are shown. Basically, CT systems of this kind and associated control devices are known to the person skilled in the art and do not need to be explained in detail therefore.

A core component of the control device 10 is here a processor 11 on which different components are implemented in the form of software modules. The control device 10 also has a terminal interface 14 to which a terminal 20 is connected via which a user can operate the control device 10 and therefore the computed tomography system 1. A further interface 15 is a network interface for connection to a data bus 21 in order to thus produce a connection to an RIS (radiology information system) or PACS (Picture Archiving and Communication System).

The scanner 2 can be controlled by the control device 10 via a control interface 13, in other words, for example, the rotational speed of the gantry, the displacement of the patient couch 5 and the X-ray source 3 itself are controlled. The raw data RD is read out from the detector 4 via an acquisition interface 12. Furthermore, the control device 10 has a storage unit 16. This storage unit 16 can comprise a database, an atlas, which contains comparison data sets V of tissue types of different body regions or compartments.

A measuring control unit 17 inter alia is implemented on the processor 11 as a software component. Via the control interface 13 this measuring control unit 17 controls the scanner 2 on the basis of one or more chosen measuring protocol(s), which were optionally modified by the user via the terminal 20, in order to carry out a measurement and to acquire data.

A further component on the processor 11 is an image data-reconstruction unit 6 with which the desired image data is reconstructed from the raw data RD obtained via the data acquisition interface 12. The image data reconstruction unit 6 is configured as an inventive device 6.

The device 6 comprises a data interface 7 configured to receive a CT data set D of an object and a comparison data set V, which are here both transmitted in the form of raw data RD. The data interface 7 is configured here as a bidirectional data interface which can both receive raw data and transmit control data, for example in order to control recording of the object O and the phantom P.

The device also comprises a contrast suppression unit 8 configured for suppressing a contrast, which has been caused by a tissue type (or by two or more different tissue types), and for generating a contrast-suppressed data set K. The suppression unit 8 contains a superimposition unit 8*a*, which is configured for creating a resulting data set R, comprising a superimposition of the contrast-suppressed data set K with the CT data set D. Furthermore, the device 6 comprises an analysis unit 9 configured for analysis of the contrast-suppressed data set R by way of a machine learning algorithm, with the analysis being configured to identify at least one change within the tissue type (or the two or more different tissue types).

In this example the analysis unit 9 is configured for the reconstruction of images in addition to analysis. Alternatively, images can also be reconstructed before suppression of the contrast. Preferably, 3D images are reconstructed.

Figure 2:
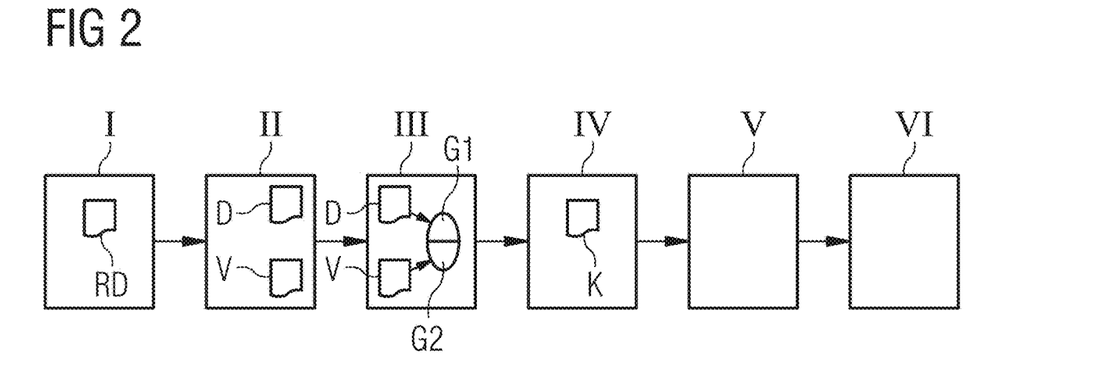
FIG. 2 shows a flowchart for one possible course of an embodiment of an inventive method.

FIG. 2 shows a flowchart for one possible course of an embodiment of an inventive method.

In step I, multispectral recording of a CT data set D and a comparison data set V in the form of raw data RD, in particular by way of a photon-counting CT system, takes place. The CT system shown in FIG. 1 can be used here.

In step II, the CT data set D of an object and of the comparison data set V, which were taken from the raw data, is provided. Here, the comparison data set V is the CT data set D of a phantom P, comprising samples, which correspond to the tissues to be examined on the object O, with provision of the comparison data set V comprising recording the phantom P within the framework of the multispectral recording method and simultaneously recording the object O.

In step III, the CT data set D is processed together with the comparison data set V by way of an iterative data reconstruction, with an identification of tissue types G1, G2 based on the CT data set being performed with the aid of the comparison data set V.

In step IV, contrasts, which have been caused by two different tissue types, are suppressed and a contrast-suppressed data set K is generated.

In step V, the contrast-suppressed data set K is analyzed by way of a machine learning algorithm, with the analysis being configured to identify at least one change within the two different tissue types G1, G2.

In step VI, the results are displayed, with different compartments preferably being displayed in different ways, for example with different colors.

Figure 3:
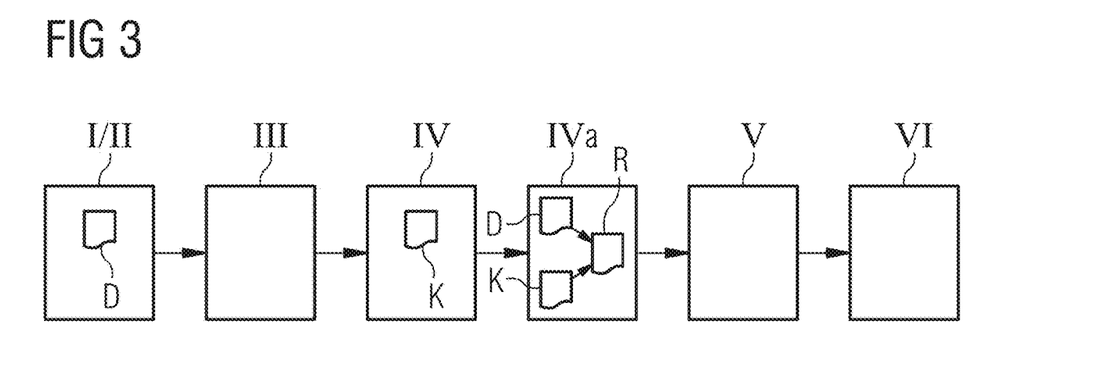
FIG. 3 shows a detailed flowchart for one possible course of an embodiment of an inventive method using the example of an examination of a stroke.

FIG. 3 shows a detailed flowchart for a possible course of an embodiment of an inventive method using the example of an examination of a stroke. In this example, the CT data set D comprises a CT scan of the brain and the tissue types G1, G2 are the gray matter and the white matter.

In the combined step I/II, a CT data set D is recorded, which is a multispectral recording of a brain of a stroke patient by way of a photon-counting CT system and provision of the CT data set D.

In step III, the CT data set D, in which a reconstruction of 3D image data from the CT data set is performed, is processed. In this example, the following steps work with the reconstructed image data and not with raw data.

In step IV, the gray-white contrast of the gray matter and of the white matter, which is stored in the contrast-suppressed data set K, is suppressed (in particular completely).

In step IVa, a resulting data set R, comprising a superimposition of the contrast-suppressed data set K and of the CT data set D, is created. Step IVa can be part of step IV.

Analysis takes place again in step V, and this is specifically configured here to identify at least one change, in particular an edema, within the white matter and/or the gray matter. The analysis can be based here on the resulting data set R.

In step VI, the results are displayed again, here in the form of 3D images, with different compartments preferably being displayed in different ways, for example with different colors.

Finally, reference is made once again to the fact that the methods described in detail above and the illustrated computed tomography system 1 are merely example embodiments which can be varied widely by the person skilled in the art without departing from the scope of the invention. Furthermore, use of the indefinite article "a" or "an" does not preclude the relevant features from also being present several times. Similarly, the terms "unit" and "module" do not preclude the relevant components from comprising a plurality of interacting subcomponents, which, optionally, can be spatially distributed also.

Although the invention has been illustrated in greater detail using the example embodiments, the invention is not limited by the disclosed examples, and a person skilled in the art can derive other variations therefrom without departing from the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for computed tomography imaging, the method comprising:
provisioning a CT data set of an object, the CT data set having been recorded via a multispectral recording method;
suppressing a contrast in the CT data set to generate a contrast-suppressed data set, wherein the contrast is caused by tissue type; and
analyzing, via a machine learning algorithm, at least one of the contrast-suppressed data set or a data set generated based on the contrast-suppressed data set, to identify at least one change in the tissue type.

2. The method of claim 1, wherein the provisioning of the CT data set of the object comprises:
recording the CT data set within a framework of the multispectral recording method using a multispectral resolving detector.

3. The method of claim 2, wherein the multispectral resolving detector is a photon-counting detector.

4. The method of claim 3, wherein the photon-counting detector allows flexible binning.

5. The method of claim 1, wherein the analyzing comprises:
determining at least one of a position of an area having a change of at least one of the tissue type or a size of the tissue type, a characteristic of the change or a progress of the change, and
wherein the analyzing is performed via the machine learning algorithm based on models from at least one of Markov models, neural networks, convolution algorithms or 3D lattice models.

6. The method of claim 1, further comprising:
provisioning a comparison data set, the comparison data set having been recorded via the multispectral recording method; and
processing the CT data set with the comparison data set via an iterative data reconstruction, wherein the processing includes performing an optimization of the CT data set based on the comparison data set.

7. The method of claim 6, wherein
the comparison data set is a CT data set of a phantom, the phantom including samples matching the tissue type of the object,
the provisioning of the comparison data set includes recording the CT data set of the phantom within a framework of the multispectral recording method, and
the CT data set of the phantom is recorded at a same time as the CT data set of the object is recorded.

8. The method of claim 1, wherein the suppressing suppresses the contrast to more than 50%, and wherein the contrast-suppressed data set includes reconstructed image data with suppressed contrast.

9. The method of claim 1, further comprising:
reconstructing three-dimensional image data from the CT data set, wherein at least one of the suppressing or the analyzing is based on the three-dimensional image data.

10. The method of claim 1, further comprising:
identifying, via iterative data processing, the tissue type based on at least one of water or fat content in the CT data set.

11. The method of claim 1, further comprising:
creating a resulting data set including a superimposition of the contrast-suppressed data set and the CT data set, wherein the analyzing is based on the resulting data set.

12. The method of claim 1, wherein
the CT data set is a multispectral recording of a brain,
the suppressing suppresses a gray-white contrast of gray matter and white matter of the brain, and the contrast-suppressed data set includes information based on the suppressing of the gray-white contrast, and
the at least one change includes at least one change within at least one of the white matter or the gray matter.

13. A non-transitory computer-readable medium storing program segments, readable and executable by at least one processor, to carry out the method of claim 1 when the program segments are executed by the at least one processor.

14. The method of claim 1, wherein the suppressing the contrast in the CT data set is based on an energy-dependent attenuation of radiation through tissue type.

15. A device for computed tomography imaging, the device comprising:
a data interface configured to receive a CT data set of an object, the CT data set having been recorded via a multispectral recording method;
a contrast suppression unit configured to suppress a contrast in the CT data set to generate a contrast-suppressed data set, wherein the contrast is caused by tissue type; and
an analysis unit configured to analyze, via a machine learning algorithm, at least one of the contrast-suppressed data set or a data set based on the contrast-suppressed data set, to identify at least one change in the tissue type.

16. A control device for controlling a computed tomography system or a diagnosis system, the control device comprising:
the device of claim 15.

17. A diagnosis system comprising:
the control device of claim 16.

18. A computed tomography system, configured to record a CT data set via a multispectral recording method, the computed tomography system comprising:
the control device of claim 16.

19. The device of claim 15, further comprising:
a superimposition unit configured to superimpose the contrast-suppressed data set with the CT data set to form a resulting data set.

20. The device of claim 19, further comprising:
an identification unit configured to identify a region in a body in which the CT data set has been recorded.

21. The device of claim 15, further comprising:
an identification unit configured to identify a region in a body in which the CT data set has been recorded.

22. The device of claim 15, further comprising:
a data interface configured to control a computed tomography system, the computed tomography system being configured to record the CT data set via the multispectral recording method.

23. The device of claim 22, wherein the computed tomography system is a dual source dual energy computed tomography system or a multi/dual source multi energy computed tomography system, configured to obtain measurements based on a photon counting method.

24. A control device, comprising:
one ore more processors; and
a memory storing computer-executable instructions that, when executed by the one or more processors, cause the control device to suppress a contrast in a CT data set of an object to generate a contrast-suppressed data set, wherein the contrast is caused by tissue type and the CT data set is recorded via a multispectral recording method, and analyze, via a machine learning algorithm, at least one of the contrast-suppressed data set or a data set generated based on the contrast-suppressed data set, to identify at least one change in the tissue type.

* * * * *